United States Patent
Tahara et al.

(10) Patent No.: US 11,544,872 B2
(45) Date of Patent: Jan. 3, 2023

(54) CAMERA CALIBRATION METHOD USING HUMAN JOINT POINTS

(71) Applicant: SONY CORPORATION, Tokyo (JP)

(72) Inventors: Daisuke Tahara, Tokyo (JP); Nobuhiro Tsunashima, Tokyo (JP)

(73) Assignee: Sony Group Corporation, Tokyo (JP)

( * ) Notice: Subject to any disclaimer, the term of this patent is extended or adjusted under 35 U.S.C. 154(b) by 596 days.

(21) Appl. No.: 16/594,385

(22) Filed: Oct. 7, 2019

(65) Prior Publication Data
US 2021/0104069 A1 Apr. 8, 2021

(51) Int. Cl.
| | | |
|---|---|---|
| G06T 7/80 | (2017.01) | |
| G06F 3/01 | (2006.01) | |
| G01B 21/04 | (2006.01) | |
| G06F 3/0484 | (2022.01) | |
| G06T 7/246 | (2017.01) | |
| G06T 7/73 | (2017.01) | |
| A61B 5/107 | (2006.01) | |
| G06T 7/00 | (2017.01) | |

(52) U.S. Cl.
CPC ............... *G06T 7/80* (2017.01); *A61B 5/107* (2013.01); *G01B 21/042* (2013.01); *G06F 3/017* (2013.01); *G06F 3/0484* (2013.01); *G06T 7/0012* (2013.01); *G06T 7/251* (2017.01); *G06T 7/73* (2017.01); *G06T 2207/10028* (2013.01)

(58) Field of Classification Search
None
See application file for complete search history.

(56) References Cited

U.S. PATENT DOCUMENTS

| | | | |
|---|---|---|---|
| 7,257,237 B1 * | 8/2007 | Luck ..................... | G06T 7/251 382/103 |
| 8,872,925 B2 | 10/2014 | Xie et al. | |
| 11,449,061 B2 * | 9/2022 | Ebrahimi Afrouzi ...... | G05D 1/0219 |
| 2014/0219550 A1 * | 8/2014 | Popa ..................... | G06V 20/42 382/154 |
| 2020/0242805 A1 * | 7/2020 | Deng ..................... | G06T 7/73 |
| 2020/0273200 A1 * | 8/2020 | Ellwein .................. | G06T 7/292 |

FOREIGN PATENT DOCUMENTS

JP          5784356 B2        7/2015

OTHER PUBLICATIONS

Puwein, Jens, "Camera Calibration and Human Estimation for Sports Broadcasts and Human Performances", ETH Zurich Research Collection,Diss. ETH No. 22207, 2014.

* cited by examiner

*Primary Examiner* — James A Thompson
(74) *Attorney, Agent, or Firm* — Haverstock & Owens, A Law Corporation

(57) ABSTRACT

A novel multiple camera calibration algorithm uses human joint points for matched key points. A recent machine-learning based human joint detector provides joint positions with labels (e.g. left wrist, right knee, and others). In single person situation, it directly provides matched key points between multiple cameras. Thus, the algorithm does not suffer a key-point matching problem, even in a very sparse camera configuration, which is challenging in the traditional image feature-based method. This algorithm provides easy setup for a multiple camera configuration for marker-less pose estimation.

21 Claims, 7 Drawing Sheets

CAMERA CALIBRATION METHOD USING HUMAN JOINT POINTS

CROSS-REFERENCE TO RELATED APPLICATION(S)

This application is related to U.S. Provisional Patent Application Ser. No. 62/792,002, filed Jan. 14, 2019 and titled, "INFORMATION PROCESSING APPARATUS, INFORMATION PROCESSING METHOD, AND PROGRAM," and U.S. Provisional Patent Application Ser. No. 62/791,998, filed Jan. 14, 2019 and titled, "INFORMATION PROCESSING APPARATUS, INFORMATION PROCESSING METHOD, AND PROGRAM," which are hereby incorporated by reference in their entireties for all purposes.

FIELD OF THE INVENTION

The present invention relates to cameras. More specifically, the present invention relates to camera calibration.

BACKGROUND OF THE INVENTION

The traditional camera calibration has the following drawback for easy-usage. It provides very accurate calibration results. But, it spends a lot of time to do so. The traditional camera calibration uses checkerboard and spends time and man-power. General objects also suffer from a matching problem.

SUMMARY OF THE INVENTION

A novel multiple camera calibration algorithm uses human joint points for matched key points. A recent machine-learning based human joint detector provides joint positions with labels (e.g. left wrist, right knee, and others). In single person situation, it directly provides matched key points between multiple cameras. Thus, the algorithm does not suffer a key-point matching problem, even in a very sparse camera configuration, which is challenging in the traditional image feature-based method. This algorithm provides easy setup for a multiple camera configuration for marker-less pose estimation.

In one aspect, a method comprises setting a plurality of cameras, moving a target around and performing camera calibration of the plurality of cameras by: collecting human joint positions in 2D images of each of the cameras by using a joint detector, fixing a gauge, estimating camera positions and orientations by minimizing a summation of triangulation errors and fitting a floor plane. The plurality of cameras are set where at least two neighboring cameras have an overlapping area. Moving the target around includes the target walking and waving arms. The target is guided by a graphical user interface. Collecting the human joint positions includes image processing to determine approximately adjoining, moving segments and an approximately, relatively stationary joint point. Fixing the gauge includes finding optimal rotation and translation between points. Fitting the floor plane includes fitting the floor plane to a distribution of ankle joint points. The method further comprises implementing human joint-based camera odometry including: detecting 2D joint positions in each fixed and moving camera by using a machine-learning based joint detector, calculating 3D joint positions by using triangulation with the fixed cameras and estimating 3D position and orientation of a moving camera by minimizing 2D reprojected error from the calculated 3D joint positions, using a computational graph algorithm for efficient computation cost.

In another aspect, an apparatus comprises a non-transitory memory for storing an application, the application for: performing camera calibration of a plurality of cameras by: collecting human joint positions in 2D images of each of the cameras by using a joint detector, fixing a gauge, estimating camera positions and orientations by minimizing a summation of triangulation errors and fitting a floor plane and a processor coupled to the memory, the processor configured for processing the application. The plurality of cameras are set where at least two neighboring cameras have an overlapping area. Performing the camera calibration includes a target moving around including the target walking and waving arms. The target is guided by a graphical user interface. Collecting the human joint positions includes image processing to determine approximately adjoining, moving segments and an approximately, relatively stationary joint point. Fixing the gauge includes finding optimal rotation and translation between points. Fitting the floor plane includes fitting the floor plane to a distribution of ankle joint points. The application is further configured for implementing human joint-based camera odometry including: detecting 2D joint positions in each fixed and moving camera by using a machine-learning based joint detector, calculating 3D joint positions by using triangulation with the fixed cameras and estimating 3D position and orientation of a moving camera by minimizing 2D reprojected error from the calculated 3D joint positions, using a computational graph algorithm for efficient computation cost.

In another aspect, a system comprises a plurality of cameras for acquiring content and a device configured for: performing camera calibration of the plurality of cameras by: collecting human joint positions in 2D images of each of the cameras by using a joint detector, fixing a gauge, estimating camera positions and orientations by minimizing a summation of triangulation errors and fitting a floor plane. The plurality of cameras are set where at least two neighboring cameras have an overlapping area. Performing the camera calibration includes a target moving around including the target walking and waving arms. The target is guided by a graphical user interface. Collecting the human joint positions includes image processing to determine approximately adjoining, moving segments and an approximately, relatively stationary joint point. Fixing the gauge includes finding optimal rotation and translation between points. Fitting the floor plane includes fitting the floor plane to a distribution of ankle joint points. The device is further configured for implementing human joint-based camera odometry including: detecting 2D joint positions in each fixed and moving camera by using a machine-learning based joint detector, calculating 3D joint positions by using triangulation with the fixed cameras and estimating 3D position and orientation of a moving camera by minimizing 2D reprojected error from the calculated 3D joint positions, using a computational graph algorithm for efficient computation cost.

DETAILED DESCRIPTION OF THE PREFERRED EMBODIMENT

The multiple camera marker-less pose estimation does not need very accurate calibrations, compared with a volumetric application, such as performance capture. For example, practical investigations show that 10 cm errors are still acceptable. Thus, the novel method has been developed with much easier and lower accurate operation. The performance target is providing visually natural results in 3D pose estimation combined with easy camera calibration.

A focus of the method is using human joints as easy-matching keypoints. Recent progress in machine learning, especially deep learning, provides higher/confident human joint detectors. They detect human joint positions on an input 2D image by using a convolutional neural network. Detection performance and localization accuracy are drastically improved.

By using joint detection on each image, it is possible to collect well-matched, not-so-accurate, but many, keypoints.

Figure 1:
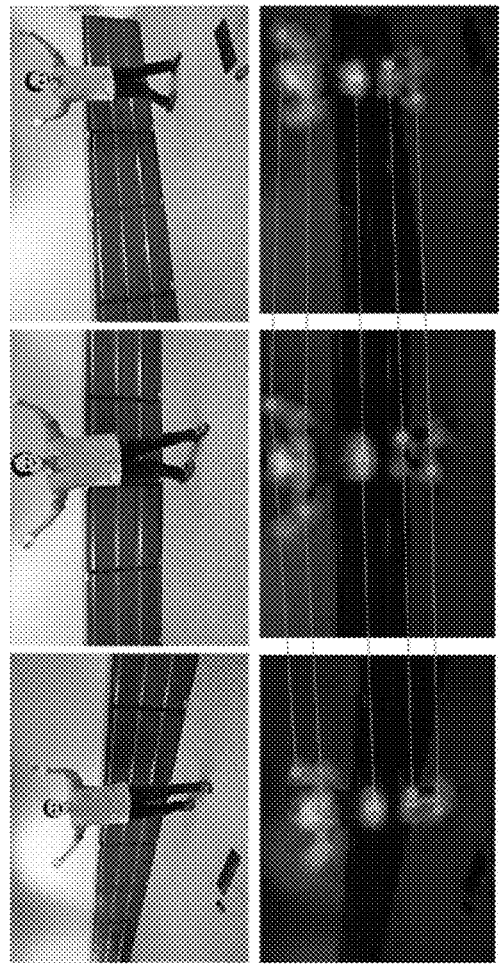
FIG. 1 illustrates examples of using joints to determine matching keypoints for camera calibration according to some embodiments.
Figure 1:
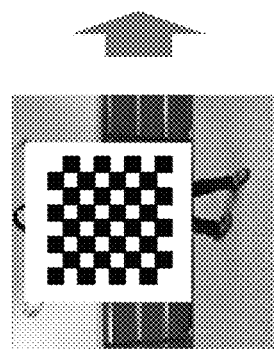

FIG. 1 illustrates examples of using joints to determine matching keypoints for camera calibration according to some embodiments. Instead of using a checkerboard pattern for calibration, joints are able to be used as described herein.

On the camera calibration algorithm, the single person scene is assumed for confirming joint-point correspondences. Namely, detected confident joints on each of the images are directly matched.

Since current Deep Learning-based Joint Detection performs very well in this application, the following table is an abstract-comparison for the designed algorithm.

|  | Checkerboard (Traditional) | Human Joint Based |
| --- | --- | --- |
| Keypoint position | Accurate | Not very accurate |
| Amount | Not many | Massive |
| Outlier point | Moderate | Few |
| Matching | Outlier-handling is necessary | Almost free from mismatching |
| Algorithm detection | Use a few, but accurate keypoints, such as 8 point algorithm | Use all densely distributed keypoints. Power of statistics suppresses errors |

The target problem structure is similar to "Bundle Adjustment." The target is providing an automatic camera calibration system. The estimating parameters are camera position and orientation. It is assumed that camera-intrinsic parameters are given.

The workflow of camera setting and calibration includes:
1. Set cameras.
2. Walk around, waving arms, in single person. Guided by Graphical User Interface (GUI) for collecting "widely distributed joint keypoints in 3D space."
3. Solve camera calibration, numerically.
4. Go to skeleton calibration.

Figure 2:
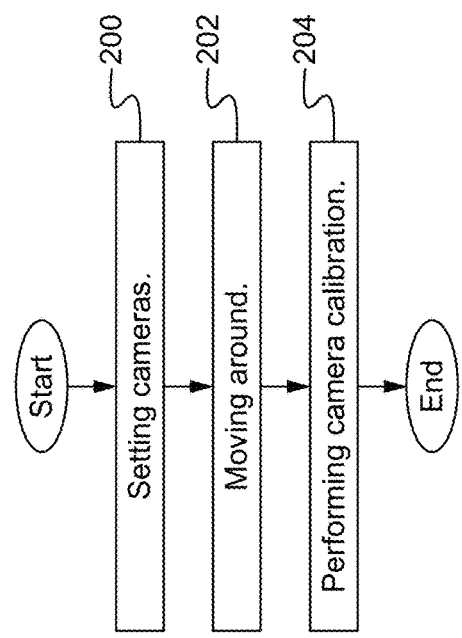
FIG. 2 illustrates a flowchart of a method of camera setting and calibration according to some embodiments.

FIG. 2 illustrates a flowchart of a method of camera setting and calibration according to some embodiments. In the step 200, a plurality of cameras are set. For example, 3 cameras are set approximately 120 degrees apart from each other. In some embodiments, the cameras are parallel with each other (e.g., 0 degrees). Therefore, the cameras are able to be any angle from each other as long as there is an overlapping section. Any number of cameras are able to be used and at any angles apart from each other. In the step 202, a target (e.g., person) moves around (e.g., walks around and waves arms). Compared with the traditional method of using a checker-board plane, the method described herein allows easy setting of cameras with a larger angle. The traditional method needs to see the checker-board plane in each camera. The method described herein uses human joints, which are able to be recognized from all 360 degrees. In some embodiments, the target is guided by a GUI which directs the target what to do. For example, the GUI is displayed on a screen and instructs the user via text, images or videos to move in certain ways such as walk, lift leg, lift right arm, lift both arms, and so on.

In the step 204, camera calibration is performed as described herein. Specifically, camera calibration includes: collect human joint positions in 2D images of each of the cameras by using a joint detector; fixing the gauge (global scale, translation, rotation); estimating camera positions and orientations by minimizing summation of triangulation errors; and fitting the floor plane. Collecting human joint positions in 2D images using a joint detector is able to be implemented in any manner such as using image processing to determine where two straight lines move and touch, and the point at which the lines touch is the joint. Furthering the example, the movement of segments (body parts) is analyzed and if the movement amount is above a threshold, that is a moving part such as a hand, forearm, upper arm, upper leg, lower leg, or foot, and points that do not move above a threshold (the threshold could be the same or different from the previous threshold), are joints. In some embodiments, additional image processing analysis is performed such as determining which direction the segments move in relation to other segments and determining where the segments meet, and if the segments move in a specified angle in relation to each other, the point at which the segments meet is a joint.

Fixing the gauge (global scale, translation, rotation) is able to involve finding an optimal rotation and translation between corresponding 3D points. For pinning translation/rotation invariance, in some embodiments, it is assumed that ankle joints should distribute just near the floor-plane, when walking around.

The "gauge" is degree of freedom in the global scale, translation and rotation. Fixing the gauge assumes the global scale, translation and rotation, which will be adjusted later by using ankle joint distribution on the floor-plane. This fixing gives the "deterministic" minimization problem, namely the triangulation-error-minimization has the single optimal camera positions and orientations.

Thus, in this gauge-fixing step, ankle joint distribution is not used. Equations (4) and (5) fix the gauge.

Estimating camera positions and orientations by minimizing summation of triangulation errors. Again, through image processing and mathematical analysis, triangulation errors are able to be determined and summed and then minimized to estimate the camera positions and orientations.

The floor plane will be fit to ankle joints distribution. Remaining one rotation degree of freedom (e.g., global rotation according to vertical axis on the floor) is adjusted manually in the application.

In some embodiments, fewer or additional steps are implemented. For example, after camera calibration, the next step is skeleton calibration. Skeleton calibration includes measuring the skeleton length, and then based on the skeleton length, the global scale is adjusted. For example, a specified ratio of the skeleton length and the global scale is maintained. In some embodiments, the order of the steps is modified.

The target performance is different from stereotypical "camera calibration." Thus, the design philosophy is as follows:
1. Do not stack on "mm"-accuracy, epipolar, . . . , distortion correction, and others.
2. Target accuracy is visually enough for 3D pose estimation.
3. Fundamentally unsolvable points should be handled by operation, e.g., manual inputs.

An overview of the camera calibration method includes:
1. Collect human joint positions on 2D images of each of the cameras by using a joint detector.
2. Fix the gauge (global scale, translation, rotation), for getting deterministic minimization problem, by assuming the gauge.
3. Estimate camera positions and orientations by minimizing summation of triangulation errors.
4. Fit floor plane, for determining global translation and rotation.
5. Measure skeleton length and adjust the global scale.

Target/Estimating parameters are camera position and orientation and 6 degrees of freedom (DoF), of multiple cameras. For smooth and minimal parameterization se(3) Lie algebra parameterization is adopted.

$$\{(x_0^n, x_1^n, x_2^n, x_3^n, x_4^n, x_5^n) \in se(3) | n \in [0:N]\} \quad (1)$$

with the number of multiple cameras N. The special Euclidean Lie algebra se(3) has 6 elements. The first 3 elements $x_0^n$, $x_1^n$, $x_2^n$ denote special orthogonal Lie algebra so(3), and the later 3 rotation elements $x_0^n$, $x_4^n$, $x_5^n$ denote translation elements $T(3) \in \mathbb{R}^3$ in 3D space, respectively.

The advantages of se(3) are as follows:
No Gimbal Locks (cf. Euler angle).
No Singular Points (cf. Polar coordinate).
No Additional Constraints, Minimum DoF (cf. Quaternion).

For practical operation, exponential mapping se(3) SE(3) is adopted for getting matrix representation.

The measured information, observables, are joint positions and confidence values on each 2D camera image. They are provided by the machine learning based joint detector.

$$\{(u_i^n, v_i^n, w_i^n, t_i^n) | i \in [0:M], n \in [0:N]\} \quad (2)$$

where $(u_i^n, v_i^n)$, $w_i^n \in [0:1]$, and $t_i^n$ denote "2D position," "confidence value," and "joint type" of i-th detected joint from n-th camera/view, respectively. For confident results, only joint positions on 2D images are used/selected, when all views are detected, simultaneously. The total number of detected joints denotes M. The "joint type" means human joint labels, such as left wrist and right elbow.

Detected joints are collected when at least two views (cameras) detect the same joint. In this case $e_i^n$ of the other/remaining views (cameras) are set to zero $w_i^n=0$, because of being undetected. Two or more views allow deterministic triangulation point.

On the other hand, when only one or fewer views (cameras) detect a joint, this joint will not be collected/accumulated into the group in equation (2).

It is assumed that the following parameters are given: camera intrinsic parameters on each multiple camera (field of view angle (focal length, screen size), aspect ratio, distortion parameters) and skeleton length between left-right-wrists.

The simple perspective camera model is adopted for bridging 2D image-plane and 3D real-space. Perspective projection-rays (with weight and label) of each detected joint points are able to be obtained by using the given camera parameters and se(3) parameters.

$$\{(e_i^n, a^n, w_i^n, t_i^n) | i \in [0:M], n \in [0:N]\}, \quad (3)$$

where $e_{\{i\}}^n = (e_{\{i,x\}}^n, e_{\{i,y\}}^n, e_{\{i,z\}}^n)$ denotes normalized directional vector of i-th joint from n-th camera in 3D, and $a^n = (a_{\{x\}}^n, a_{\{y\}}^n, a_{\{z\}}^n)$ denotes n-th camera position in 3D.

Gauge freedom/invariance—scaling and absolute-positioning—should be handled by combining some assumptions:

The freedom/invariance is not judged "Is this world mm-scale or inch-scale?" by only using information from pin-hole camera views. In comparison, stereo-camera solves it by using camera parameters and given "base-line."

The system is not pinned to absolute coordinates—global-translation and rotation invariance.

For pinning translation/rotation invariance, it is assumed that ankle joints should distribute just near the floor-plane, when walking around. Thus, the floor-plane will be fit to ankle joints distribution. Remaining one rotation degree of freedom (e.g., global rotation according to vertical axis on the floor) is adjusted manually in the application.

For pinning scale invariance, the pre-input person skeleton length is used, especially length between left wrist and right wrist. 3D joint points of left/right wrists, elbows, shoulders, and necks are able to be obtained from triangulation, which is explained later. Thus, T-pose (horizontally strait in both arms) is able to be recognized and measured the above length. T-pose allows the length between the left wrist and right wrist to be measured, namely summation of lengths on left lower arm, left upper arm, left-to-right shoulder, right upper arm, right lower arm.

In order to improve the robustness, several samples are accumulated. Scale gauge is adjusted by scaling average value of left-right-wrist-distance to pre-input length. For example, "Mr. James is 136 cm in left-right-wrists." Obviously, other lengths are able to be used, such as human height, for scale pinning.

In order to keep deterministic problems at the camera position and orientation estimation, the global gauge is fixed by fixing the following values. The 0-th camera position and orientation is fixed to some 3D point and direction.

$$(x_{0,0}, x_1^0, x_2^0, x_3^0, x_4^0, x_5^0) = (0,0,0,0,0,0) \quad (4)$$

And, the relative x-axis distance between the 0-th and 1-st cameras is fixed such as:

$$x^1{}_3 = 1. \quad (5)$$

The above is well known as 'trivial gauge fixing' in bundle adjustment.

Camera Position and Orientation Estimation

The summation of squared residual error of weighted least square triangulation is minimized.

$$\{x \text{ without gauge-fixed elements}\} = \operatorname*{argmin} \sum_{i=0}^{M-1} D_i^2, \quad (6)$$

where $D_1^2$ is the residual error of i-th joint and given as $$D_i^2 = \sum_{n=0}^{N-1} w_i^n \left[ \|p_i - a^n\|^2 - \{e_i^n \cdot (p_i^n - a^n)\}^2 \right] \quad (7)$$

$$= \sum_{n=0}^{N-1} w_i^n \left[ \sum_{j=x,y,z} (p_{i,j} - a_j^n)^2 - \sum_{j=x,y,z} \{e_{i,j}^n \cdot (p_{i,j}^n - a_j^n)\}^2 \right].$$

The 3D point $p_i = p_{\{i,x\}}, p_{\{i,y\}}, p_{\{i,z\}}$, is the weighted-least-square-optimal triangulated 3D point and it is given by the stationary-condition $$0 = \frac{\partial D_i^2}{\partial p_{i,j}} = \sum_{n=0}^{N-1} w_i^n \left[ 2(p_{i,j} - a_j^n) - 2 \sum_{k=x,y,z} e_{i,k}^n (x_{i,k}^n - a_k^n) e_{i,j}^n \right] \quad (8)$$

which is able to be solved analytically by following a 3×3 linear system $A_i p_i = b_i$ with $$A_{kl}^i = \sum_{n=0}^{N-1} w_i^n (e_{i,k}^n e_{i,l}^n - \delta_{kl}), \; b_{i,k} = \sum_{n=0}^{N-1} w_i^n \sum_l a_{i,l}^n (e_{i,l}^n e_{i,k}^n - a_k^n) \quad (9)$$

Although this minimization problem is non-linear, elements are all differentiable.

Exponential map se(3) SE(3) has a closed form.

Matrix and vector operations are differentiable.

Linear system equation Ax=b has a fixed size (e.g., 3×3) and the closed form can be derived by using Cramer's rule and matrix determinant.

Thus, it can be efficiently minimized by constructing a computational graph, using auto-differentiation.

Re-projection error minimization is not stable in this case, since the number of key points is sparser than the typical case of bundle adjustment. In addition, the keypoint accuracy and camera projection model are not so accurate for reprojection error minimization.

A frequently used algorithm in camera calibration is an 8-point algorithm and RANSAC strategy. This stands on the philosophy that there should be several accurate key points, and if they are selected, the 8-point or matrix decomposition works mathematically. On the other hand, the strategy is to minimize the weighted sum of massive residual errors. A macroscopic number of keypoints should guide to an applicable result.

Figure 3A:
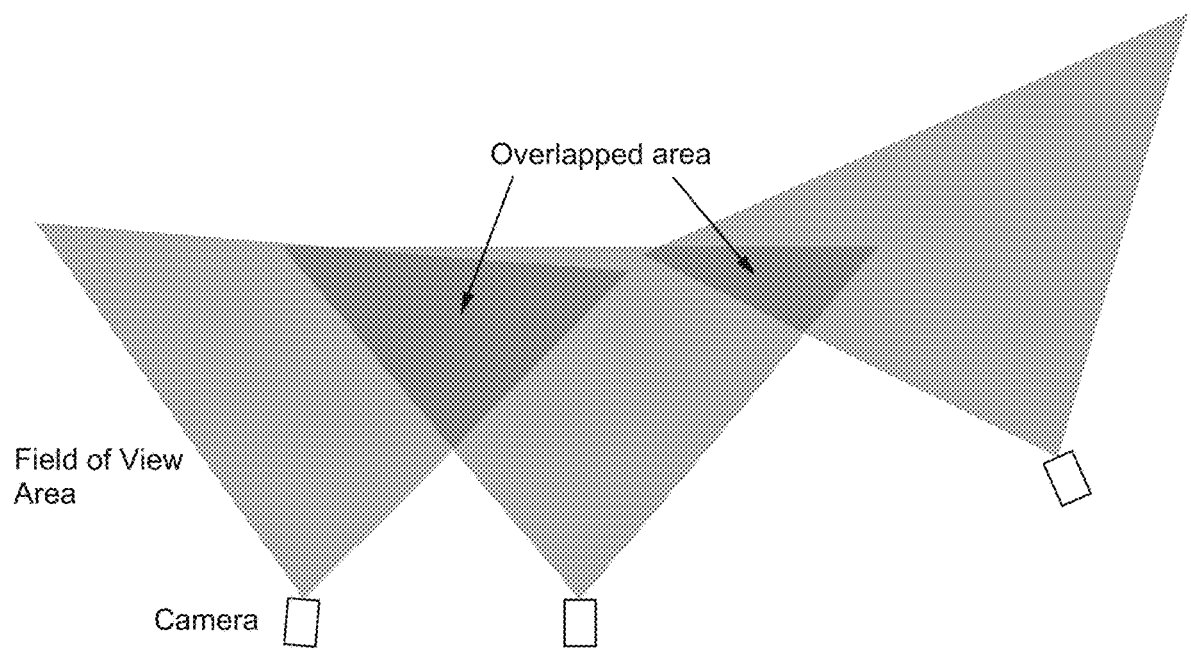
FIGS. 3A and 3B illustrate a plurality of cameras with overlapping conditions according to some embodiments.
Figure 3B:
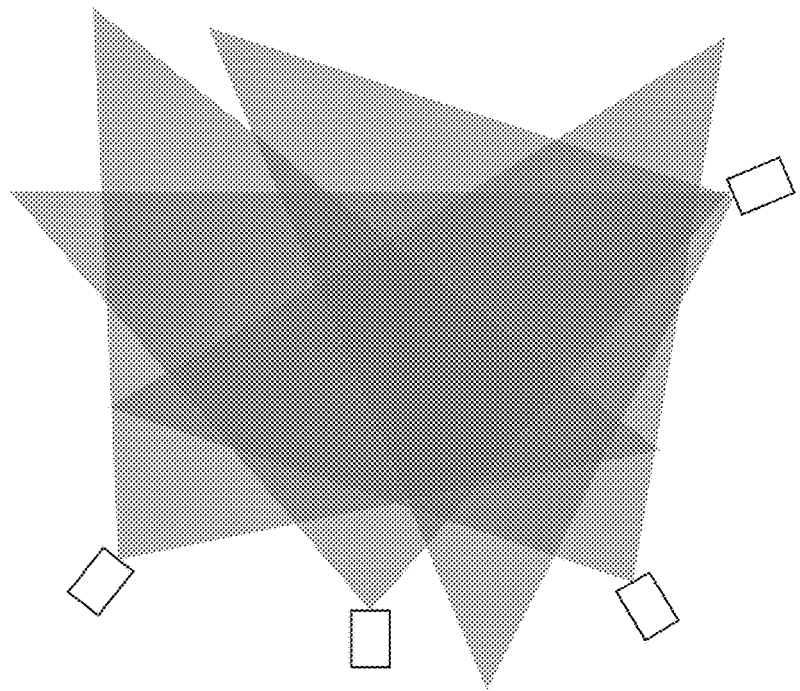

FIGS. 3A and 3B illustrate a plurality of cameras with overlapping conditions according to some embodiments. FIG. 3A shows a plurality of cameras where there are two overlapping areas including one area formed where the angle between two neighboring cameras is zero (0) degrees. FIG. 3B shows a plurality of cameras where all four (4) cameras have a common overlapping area.

Figure 4:
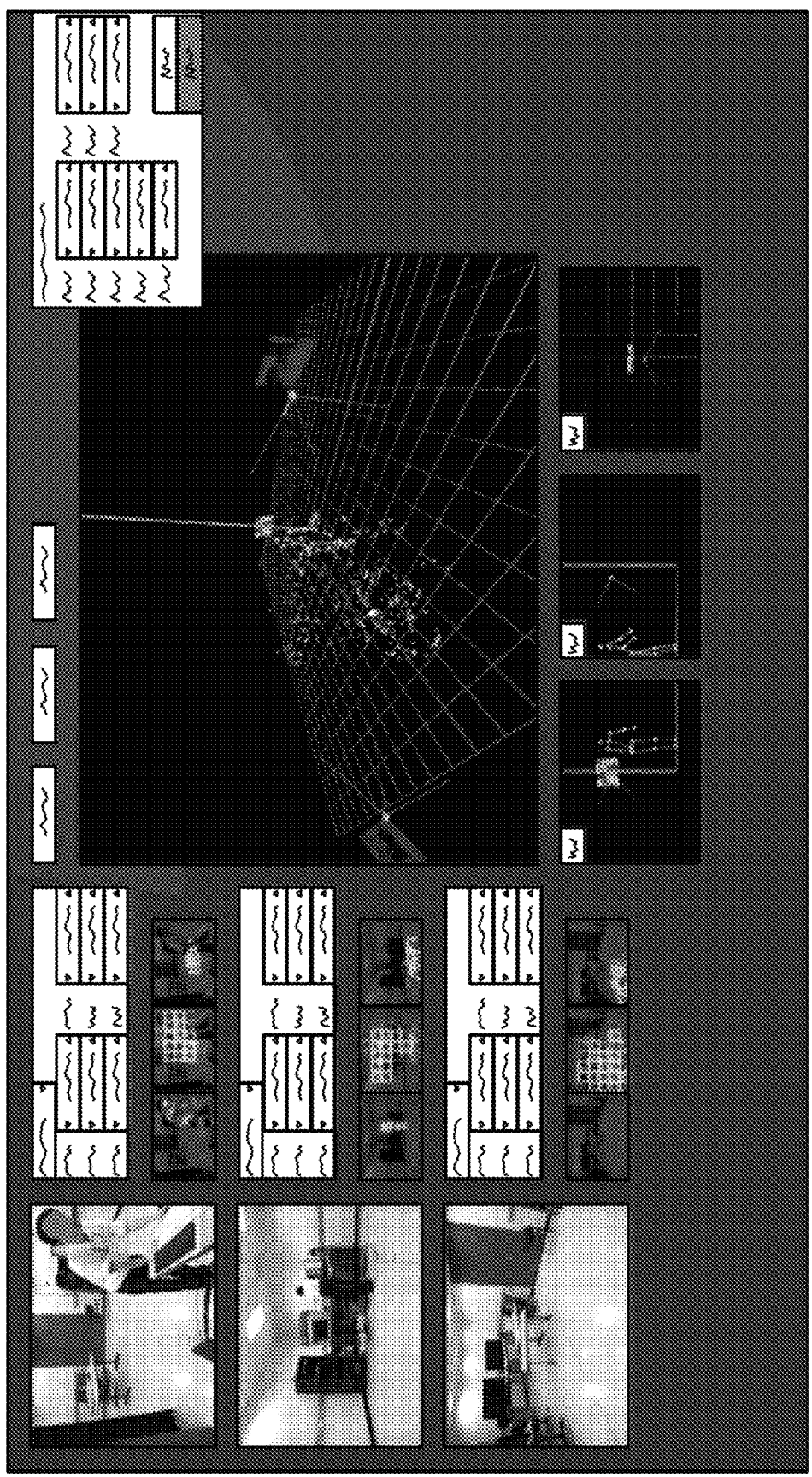
FIG. 4 illustrates results of implementing the method according to some embodiments.

FIG. 4 illustrates results of implementing the method according to some embodiments. The points at the right, large 3D view in FIG. 4 denote triangulated keypoints of whole-body for triangulation and floor plane estimation.

3 Cameras with Large Angles

The algorithm works even in this very challenging configuration in a traditional method, e.g., small overlap, large angles.

6 Cameras

Figure 5:
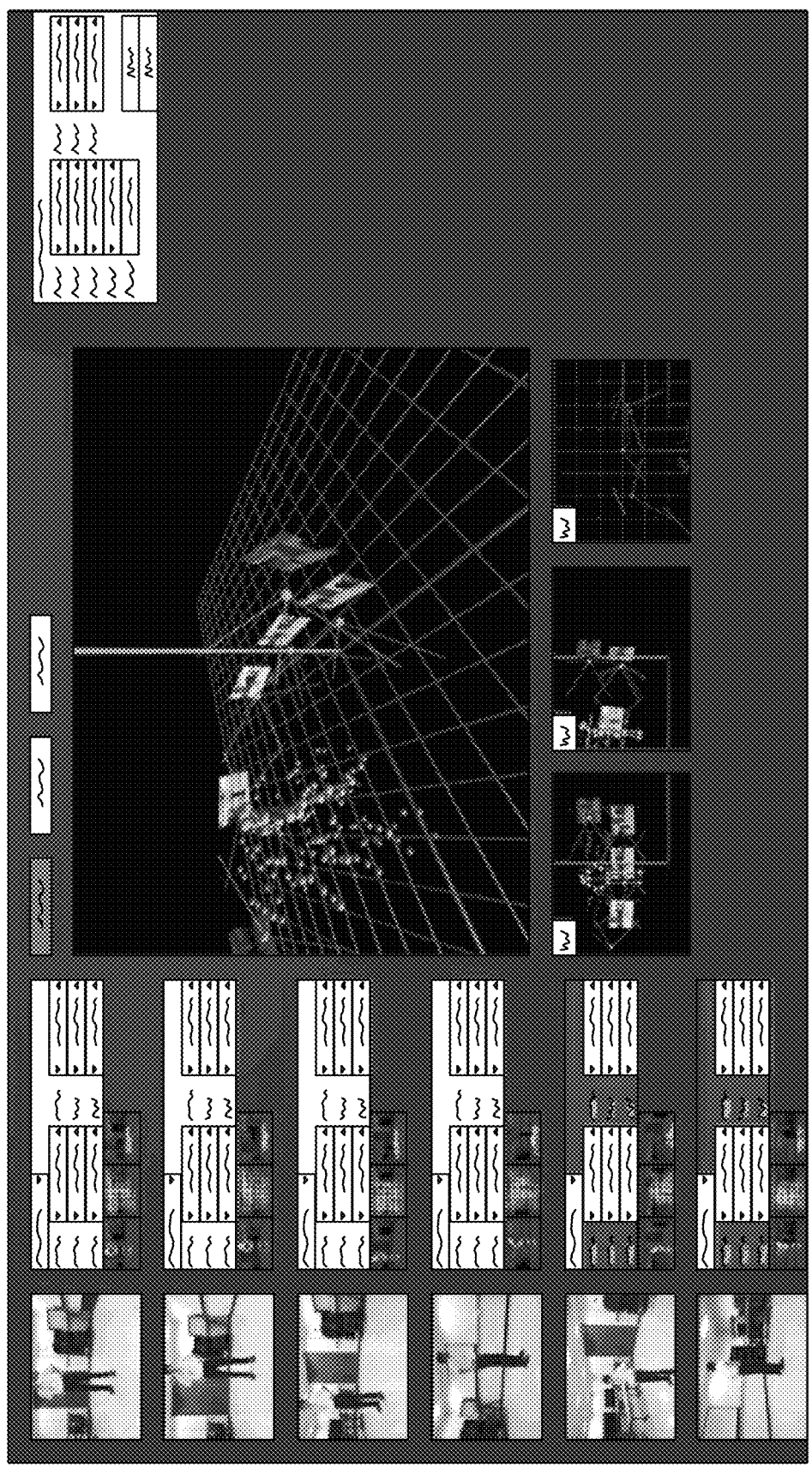
FIG. 5 illustrates an example using six cameras according to some embodiments.

FIG. 5 illustrates an example using six cameras according to some embodiments.

Human Joint-Based Camera Odometry

Moving camera position and orientation are estimated in the environment with multiple fixed cameras and a person. The key idea is using human joint points for key points in 3D space. Calibrated fixed multiple cameras estimate human joint 3D positions in real-time. The moving camera position and orientation are estimated geometrically with these points in real-time. Traditional visual odometry methods, such as keypoint-based and intensity-based methods, need texture/structure in the background. But, the method described herein works even in texture-less background, such as chromakey studio (green-flat background studio), since just human joints are used.

Figure 6:
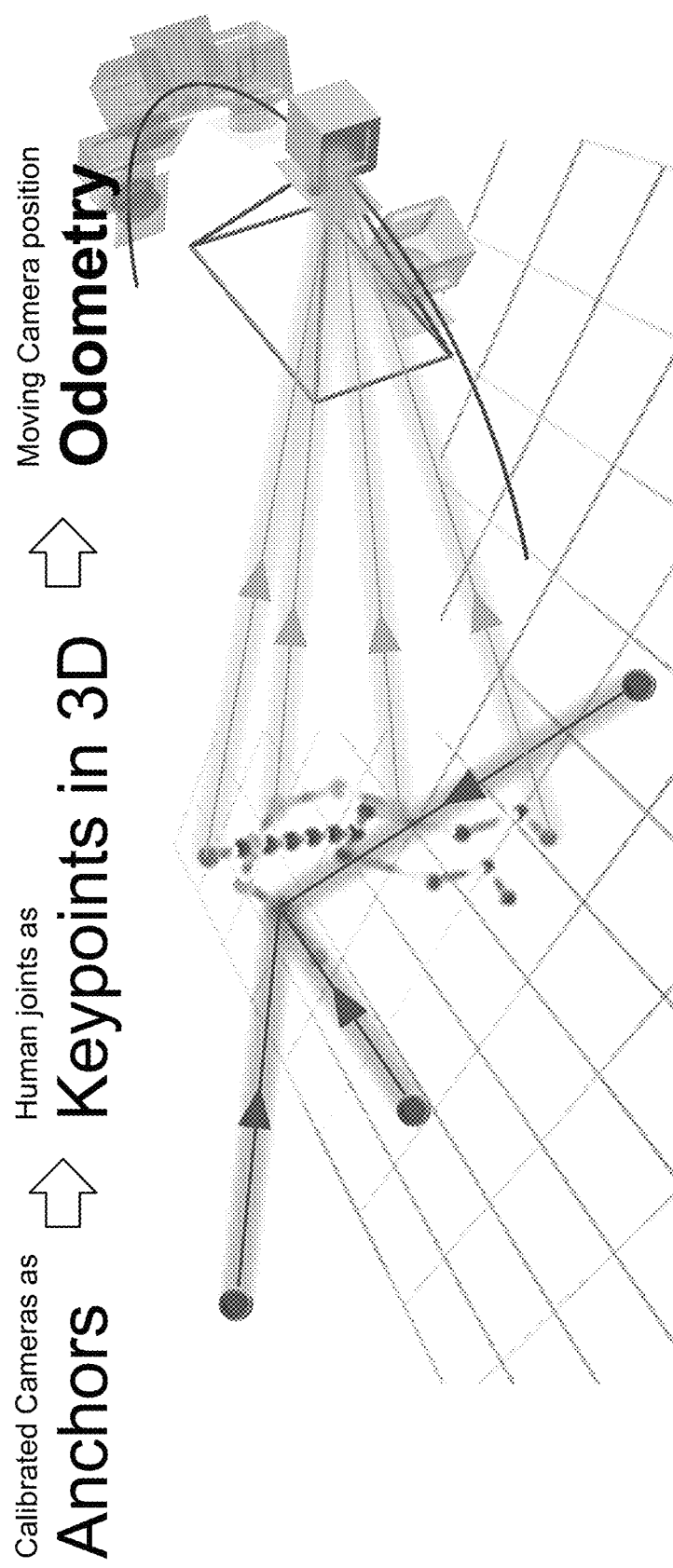
FIG. 6 illustrates a diagram of human joint-based camera odometry according to some embodiments.

FIG. 6 illustrates a diagram of human joint-based camera odometry according to some embodiments. Human joint-based camera odometry includes: detecting 2D joint positions in each fixed and moving camera by using a machine-learning based joint detector; calculating 3D joint positions by using triangulation with the fixed cameras; and estimating 3D position and orientation of a moving camera by minimizing 2D reprojected error from the calculated 3D joint positions, using a computational graph algorithm for efficient computation cost.

Figure 7:
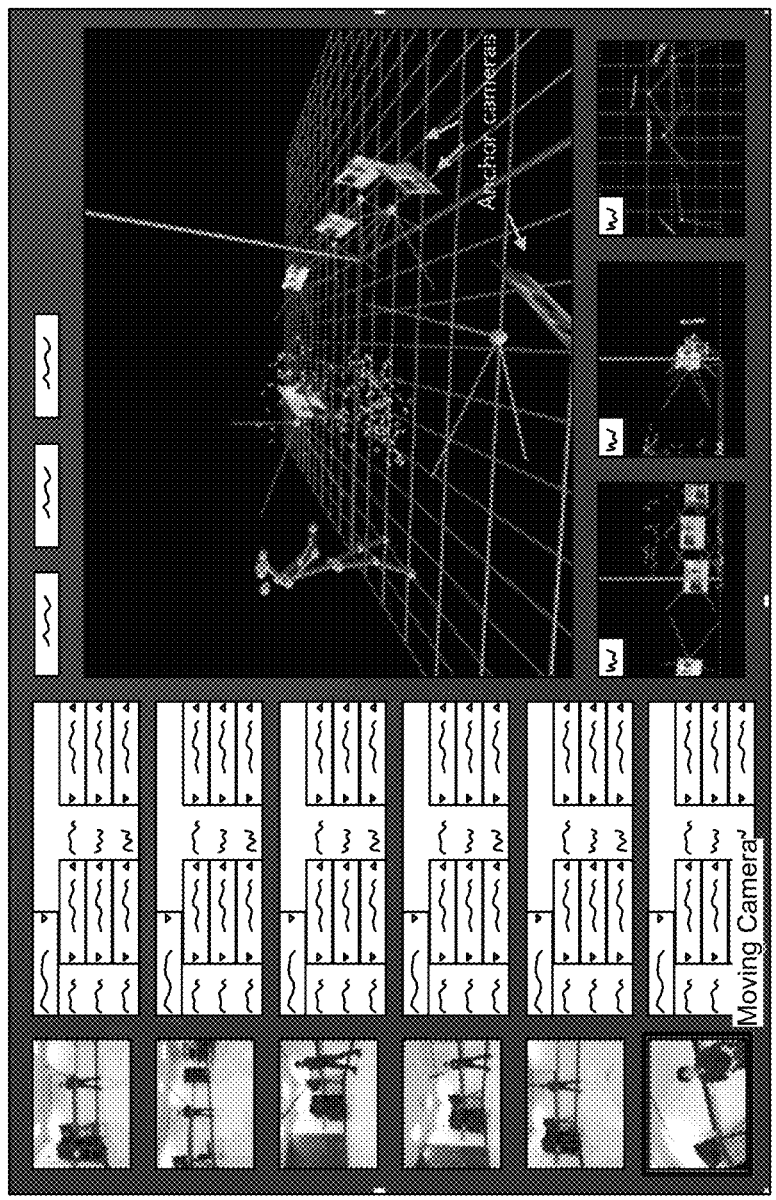
FIG. 7 illustrates exemplary results in real-time according to some embodiments.
Figure 7:
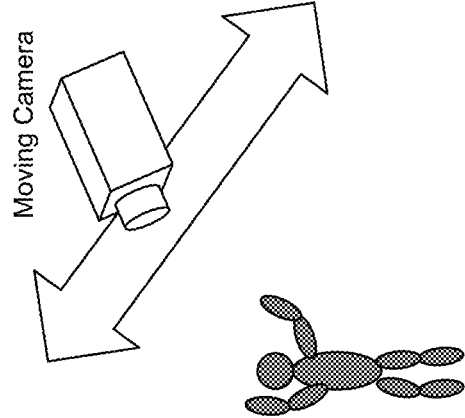

FIG. 7 illustrates exemplary results in real-time according to some embodiments. The algorithm works in real-time.

Figure 8:
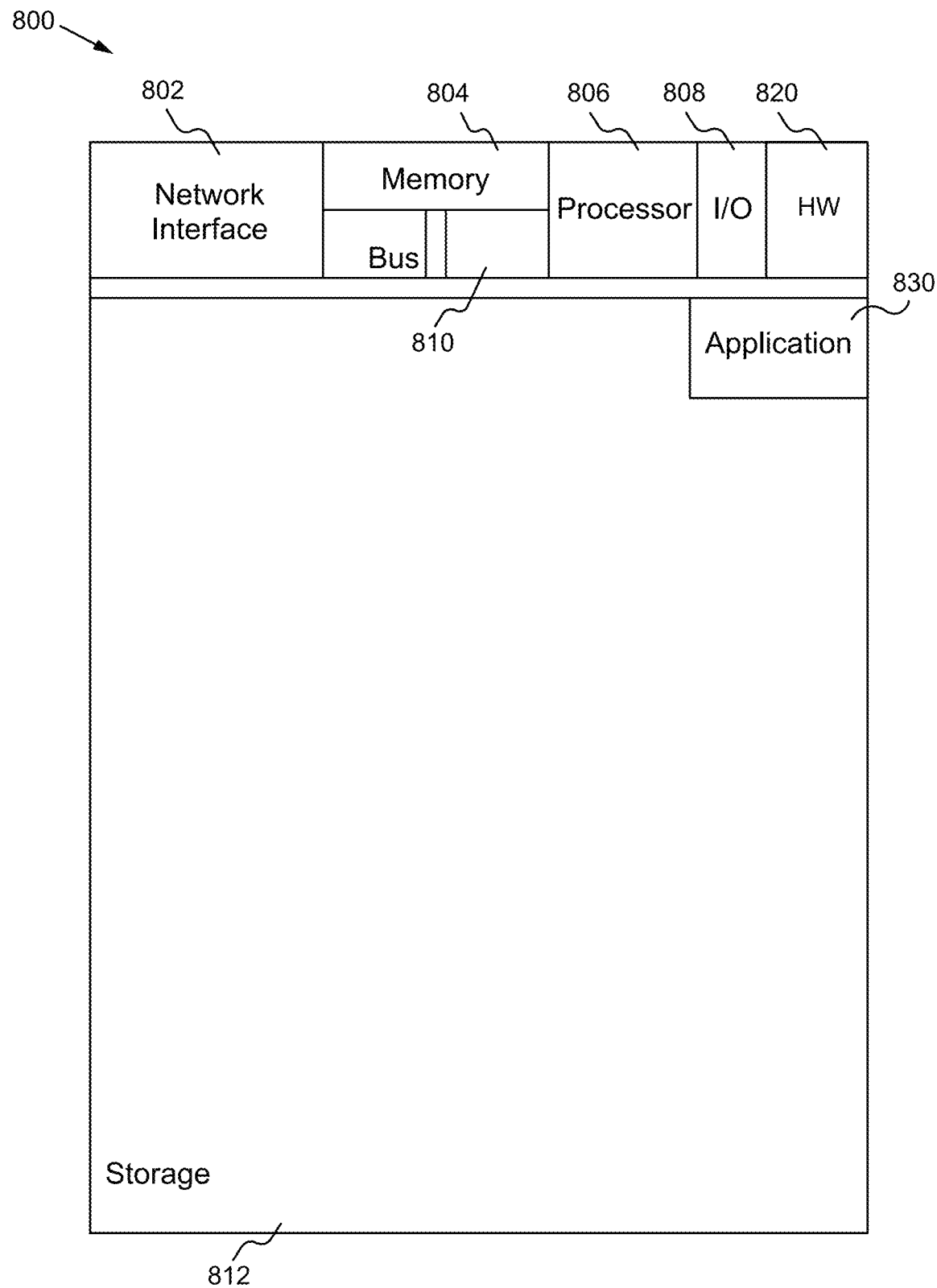
FIG. 8 illustrates a block diagram of an exemplary computing device configured to implement the camera calibration method according to some embodiments.

FIG. 8 illustrates a block diagram of an exemplary computing device configured to implement the camera calibration method according to some embodiments. The computing device 800 is able to be used to acquire, store, compute, process, communicate and/or display information such as images and videos including 3D content. The computing device 800 is able to implement any of the camera calibration method aspects. In general, a hardware structure suitable for implementing the computing device 800 includes a network interface 802, a memory 804, a processor 806, I/O device(s) 808, a bus 810 and a storage device 812. The choice of processor is not critical as long as a suitable processor with sufficient speed is chosen. The memory 804 is able to be any conventional computer memory known in the art. The storage device 812 is able to include a hard drive, CDROM, CDRW, DVD, DVDRW, High Definition disc/drive, ultra-HD drive, flash memory card or any other storage device. The computing device 800 is able to include one or more network interfaces 802. An example of a network interface includes a network card connected to an Ethernet or other type of LAN. The I/O device(s) 808 are able to include one or more of the following: keyboard, mouse, monitor, screen, printer, modem, touchscreen, button interface and other devices. Camera calibration application(s) 830 used to implement the camera calibration method are likely to be stored in the storage device 812 and memory 804 and processed as applications are typically processed. More or fewer components shown in FIG. 8 are able to be included in the computing device 800. In some embodiments, camera calibration hardware 820 is included. Although the computing device 800 in FIG. 8 includes applications 830 and hardware 820 for the camera calibration method, the camera calibration method is able to be implemented on a computing device in hardware, firmware, software or any combination thereof. For example, in some embodiments, the camera calibration applications 830 are programmed in a memory and executed using a processor. In another example, in some embodiments, the camera calibration hardware 820 is programmed hardware logic including gates specifically designed to implement the camera calibration method.

In some embodiments, the camera calibration application(s) 830 include several applications and/or modules. In some embodiments, modules include one or more sub-modules as well. In some embodiments, fewer or additional modules are able to be included.

In some embodiments, the camera calibration hardware 820 includes camera components such as a lens, an image sensor, and/or any other camera components.

Examples of suitable computing devices include a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player (e.g., DVD writer/player, high definition disc writer/player, ultra high definition disc writer/player), a television, a home entertainment system, an augmented reality device, a virtual reality device, smart jewelry (e.g., smart watch), a vehicle (e.g., a self-driving vehicle) or any other suitable computing device.

To utilize the camera calibration method, a device acquires or receives 2D or 3D content and processes the content and performs the camera calibration as described herein. The camera calibration method is able to be implemented with user assistance or automatically without user involvement.

In operation, the camera calibration method enables efficient calibration of a camera. The multiple camera markerless pose estimation does not need very accurate calibrations, compared with a volumetric application, such as performance capture. For example, practical investigations show that 10 cm errors are still acceptable. Thus, the novel method has been developed with much easier and lower accurate operation. The performance target is providing visually natural results in 3D pose estimation combined with easy camera calibration.

Some Embodiments of Camera Calibration Method Using Human Joint Points

1. A method comprising:
   setting a plurality of cameras;
   moving a target around; and
   performing camera calibration of the plurality of cameras by:
   collecting human joint positions in 2D images of each of the cameras by using a joint detector;
   fixing a gauge;
   estimating camera positions and orientations by minimizing a summation of triangulation errors; and
   fitting a floor plane.
2. The method of clause 1 wherein the plurality of cameras are set where at least two neighboring cameras have an overlapping area.
3. The method of clause 1 wherein moving the target around includes the target walking and waving arms.
4. The method of clause 1 wherein the target is guided by a graphical user interface.
5. The method of clause 1 wherein collecting the human joint positions includes image processing to determine approximately adjoining, moving segments and an approximately, relatively stationary joint point.
6. The method of clause 1 wherein fixing the gauge includes finding optimal rotation and translation between points.
7. The method of clause 1 wherein fitting the floor plane includes fitting the floor plane to a distribution of ankle joint points.
8. The method of clause 1 further comprising implementing human joint-based camera odometry including:
   detecting 2D joint positions in each fixed and moving camera by using a machine-learning based joint detector;
   calculating 3D joint positions by using triangulation with the fixed cameras; and
   estimating 3D position and orientation of a moving camera by minimizing 2D reprojected error from the calculated 3D joint positions, using a computational graph algorithm for efficient computation cost.
9. An apparatus comprising:
   a non-transitory memory for storing an application, the application for:
   performing camera calibration of a plurality of cameras by:
   collecting human joint positions in 2D images of each of the cameras by using a joint detector;
   fixing a gauge;
   estimating camera positions and orientations by minimizing a summation of triangulation errors; and
   fitting a floor plane; and
   a processor coupled to the memory, the processor configured for processing the application.
10. The apparatus of clause 9 wherein the plurality of cameras are set where at least two neighboring cameras have an overlapping area.
11. The apparatus of clause 9 wherein performing the camera calibration includes a target moving around including the target walking and waving arms.
12. The apparatus of clause 11 wherein the target is guided by a graphical user interface.
13. The apparatus of clause 9 wherein collecting the human joint positions includes image processing to determine approximately adjoining, moving segments and an approximately, relatively stationary joint point.
14. The apparatus of clause 9 wherein fixing the gauge includes finding optimal rotation and translation between points.
15. The apparatus of clause 9 wherein fitting the floor plane includes fitting the floor plane to a distribution of ankle joint points.
16. The apparatus of clause 9 wherein the application is further configured for implementing human joint-based camera odometry including:
   detecting 2D joint positions in each fixed and moving camera by using a machine-learning based joint detector;
   calculating 3D joint positions by using triangulation with the fixed cameras; and
   estimating 3D position and orientation of a moving camera by minimizing 2D reprojected error from the calculated 3D joint positions, using a computational graph algorithm for efficient computation cost.

17. A system comprising:
   a plurality of cameras for acquiring content; and
   a device configured for:
   performing camera calibration of the plurality of cameras by:
   collecting human joint positions in 2D images of each of the cameras by using a joint detector;
   fixing a gauge;
   estimating camera positions and orientations by minimizing a summation of triangulation errors; and
   fitting a floor plane.
18. The system of clause 17 wherein the plurality of cameras are set where at least two neighboring cameras have an overlapping area.
19. The system of clause 17 wherein performing the camera calibration includes a target moving around including the target walking and waving arms.
20. The system of clause 19 wherein the target is guided by a graphical user interface.
21. The system of clause 17 wherein collecting the human joint positions includes image processing to determine approximately adjoining, moving segments and an approximately, relatively stationary joint point.
22. The system of clause 17 wherein fixing the gauge includes finding optimal rotation and translation between points.
23. The system of clause 17 wherein fitting the floor plane includes fitting the floor plane to a distribution of ankle joint points.
24. The system of clause 17 wherein the device is further configured for implementing human joint-based camera odometry including:
   detecting 2D joint positions in each fixed and moving camera by using a machine-learning based joint detector;
   calculating 3D joint positions by using triangulation with the fixed cameras; and
   estimating 3D position and orientation of a moving camera by minimizing 2D reprojected error from the calculated 3D joint positions, using a computational graph algorithm for efficient computation cost.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:
1. A method comprising:
   setting a plurality of cameras;
   moving a target around; and
   performing camera calibration of the plurality of cameras by:
   collecting human joint positions in 2D images of each of the cameras by using a joint detector, wherein collecting the human joint positions includes image processing to determine approximately adjoining, moving segments and an approximately, relatively stationary joint point, wherein determining the approximately adjoining, moving segments and the approximately, relatively stationary joint point includes analyzing movement of segments to determine if an amount of movement of a segment is above a threshold, and when the amount of movement of the segment is above the threshold, then the segment is a moving part, and if the amount of movement of a point is below the threshold, then the point is a joint;
   fixing a gauge;
   estimating camera positions and orientations by minimizing a summation of triangulation errors; and
   fitting a floor plane.
2. The method of claim 1 wherein the plurality of cameras are set where at least two neighboring cameras have an overlapping area.
3. The method of claim 1 wherein moving the target around includes the target walking and waving arms.
4. The method of claim 1 wherein the target is guided by a graphical user interface.
5. The method of claim 1 wherein fixing the gauge includes finding optimal rotation and translation between points.
6. The method of claim 1 wherein fitting the floor plane includes fitting the floor plane to a distribution of ankle joint points.
7. The method of claim 1 further comprising implementing human joint-based camera odometry including:
   detecting 2D joint positions in each fixed and moving camera by using a machine-learning based joint detector;
   calculating 3D joint positions by using triangulation with the fixed cameras; and
   estimating 3D position and orientation of a moving camera by minimizing 2D reprojected error from the calculated 3D joint positions, using a computational graph algorithm for efficient computation cost.
8. An apparatus comprising:
   a non-transitory memory for storing an application, the application for:
   performing camera calibration of a plurality of cameras by:
      collecting human joint positions in 2D images of each of the cameras by using a joint detector, wherein collecting the human joint positions includes image processing to determine approximately adjoining, moving segments and an approximately, relatively stationary joint point, wherein determining the approximately adjoining, moving segments and the approximately, relatively stationary joint point includes analyzing movement of segments to determine if an amount of movement of a segment is above a threshold, and when the amount of movement of the segment is above the threshold, then the segment is a moving part, and if the amount of movement of a point is below the threshold, then the point is a joint;
      fixing a gauge;
      estimating camera positions and orientations by minimizing a summation of triangulation errors; and
      fitting a floor plane; and
   a processor coupled to the memory, the processor configured for processing the application.
9. The apparatus of claim 8 wherein the plurality of cameras are set where at least two neighboring cameras have an overlapping area.
10. The apparatus of claim 8 wherein performing the camera calibration includes a target moving around including the target walking and waving arms.

11. The apparatus of claim 10 wherein the target is guided by a graphical user interface.

12. The apparatus of claim 8 wherein fixing the gauge includes finding optimal rotation and translation between points.

13. The apparatus of claim 8 wherein fitting the floor plane includes fitting the floor plane to a distribution of ankle joint points.

14. The apparatus of claim 8 wherein the application is further configured for implementing human joint-based camera odometry including:
    detecting 2D joint positions in each fixed and moving camera by using a machine-learning based joint detector;
    calculating 3D joint positions by using triangulation with the fixed cameras; and
    estimating 3D position and orientation of a moving camera by minimizing 2D reprojected error from the calculated 3D joint positions, using a computational graph algorithm for efficient computation cost.

15. A system comprising:
    a plurality of cameras for acquiring content; and
    a device configured for:
        performing camera calibration of the plurality of cameras by:
        collecting human joint positions in 2D images of each of the cameras by using a joint detector, wherein collecting the human joint positions includes image processing to determine approximately adjoining, moving segments and an approximately, relatively stationary joint point, wherein determining the approximately adjoining, moving segments and the approximately, relatively stationary joint point includes analyzing movement of segments to determine if an amount of movement of a segment is above a threshold, and when the amount of movement of the segment is above the threshold, then the segment is a moving part, and if the amount of movement of a point is below the threshold, then the point is a joint;
        fixing a gauge;
        estimating camera positions and orientations by minimizing a summation of triangulation errors; and
        fitting a floor plane.

16. The system of claim 15 wherein the plurality of cameras are set where at least two neighboring cameras have an overlapping area.

17. The system of claim 15 wherein performing the camera calibration includes a target moving around including the target walking and waving arms.

18. The system of claim 17 wherein the target is guided by a graphical user interface.

19. The system of claim 15 wherein fixing the gauge includes finding optimal rotation and translation between points.

20. The system of claim 15 wherein fitting the floor plane includes fitting the floor plane to a distribution of ankle joint points.

21. The system of claim 15 wherein the device is further configured for implementing human joint-based camera odometry including:
    detecting 2D joint positions in each fixed and moving camera by using a machine-learning based joint detector;
    calculating 3D joint positions by using triangulation with the fixed cameras; and
    estimating 3D position and orientation of a moving camera by minimizing 2D reprojected error from the calculated 3D joint positions, using a computational graph algorithm for efficient computation cost.

* * * * *